United States Patent
Choi et al.

(10) Patent No.: US 10,631,827 B2
(45) Date of Patent: Apr. 28, 2020

(54) METHOD AND APPARATUS FOR PROCESSING MEDICAL IMAGE

(71) Applicant: Samsung Electronics Co., Ltd., Suwon-si (KR)

(72) Inventors: Ji-young Choi, Suwon-si (KR); Kyoung-yong Lee, Hwaseong-si (KR); Duhgoon Lee, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/782,796

(22) Filed: Oct. 12, 2017

(65) Prior Publication Data

US 2018/0103930 A1 Apr. 19, 2018

(30) Foreign Application Priority Data

Oct. 13, 2016 (KR) .................. 10-2016-0133075

(51) Int. Cl.
| | | |
|---|---|---|
| *A61B 8/08* | (2006.01) | |
| *A61B 6/03* | (2006.01) | |
| *A61B 6/00* | (2006.01) | |
| *A61B 5/00* | (2006.01) | |
| *A61B 8/00* | (2006.01) | |

(52) U.S. Cl.
CPC ............ *A61B 8/5207* (2013.01); *A61B 6/032* (2013.01); *A61B 6/5264* (2013.01); *A61B 6/5294* (2013.01); *A61B 8/5276* (2013.01); *A61B 5/0013* (2013.01); *A61B 6/50* (2013.01); *A61B 6/503* (2013.01); *A61B 6/5211* (2013.01); *A61B 6/545* (2013.01); *A61B 8/463* (2013.01); *G06T 2207/10081* (2013.01)

(58) Field of Classification Search
CPC combination set(s) only.
See application file for complete search history.

(56) References Cited

U.S. PATENT DOCUMENTS

| | | | |
|---|---|---|---|
| 8,761,478 B2 | 6/2014 | Hsieh et al. | |
| 2004/0136490 A1* | 7/2004 | Edic | ........ A61B 6/032 378/4 |
| 2005/0041842 A1* | 2/2005 | Frakes | ........ G06K 9/3216 382/128 |

(Continued)

FOREIGN PATENT DOCUMENTS

| | | |
|---|---|---|
| EP | 2910190 A1 | 8/2015 |
| JP | 2012034972 A | 2/2012 |

(Continued)

OTHER PUBLICATIONS

European Search Report dated Apr. 12, 2018 in connection with European Patent Application No. EP 17 19 5380.

*Primary Examiner* — Tsung Yin Tsai

(57) ABSTRACT

Provided are a method and apparatus for processing a medical image. The apparatus includes: a data obtainer configured to obtain raw data generated by imaging an object; and a processor configured to determine motion correction parameters used to reconstruct an image to be used to obtain motion information based on motion characteristics of the object, obtain the motion information by using the image reconstructed based on the determined motion correction parameters, and reconstruct a tomography image from the raw data by using the motion information.

18 Claims, 12 Drawing Sheets

(56) References Cited

U.S. PATENT DOCUMENTS

| | | | |
|---|---|---|---|
| 2008/0107229 A1* | 5/2008 | Thomas | A61B 6/032 378/4 |
| 2011/0293155 A1 | 12/2011 | Nakanishi et al. | |
| 2015/0063534 A1* | 3/2015 | Allmendinger | A61B 6/032 378/19 |
| 2015/0243045 A1* | 8/2015 | Ra | A61B 6/032 382/131 |
| 2016/0055647 A1* | 2/2016 | Fujiwara | A61B 5/1121 382/103 |
| 2016/0171726 A1* | 6/2016 | Nam | G06T 11/006 382/131 |
| 2016/0225170 A1* | 8/2016 | Rifu | G06T 11/005 |

FOREIGN PATENT DOCUMENTS

| | | |
|---|---|---|
| JP | 2012152446 A | 8/2012 |
| KR | 20160045662 A | 4/2016 |
| KR | 10-1636041 B1 | 6/2016 |
| KR | 10-2017-0017156 A | 2/2017 |
| WO | 2015/126189 A1 | 8/2015 |
| WO | 2017/023105 A1 | 2/2017 |

* cited by examiner

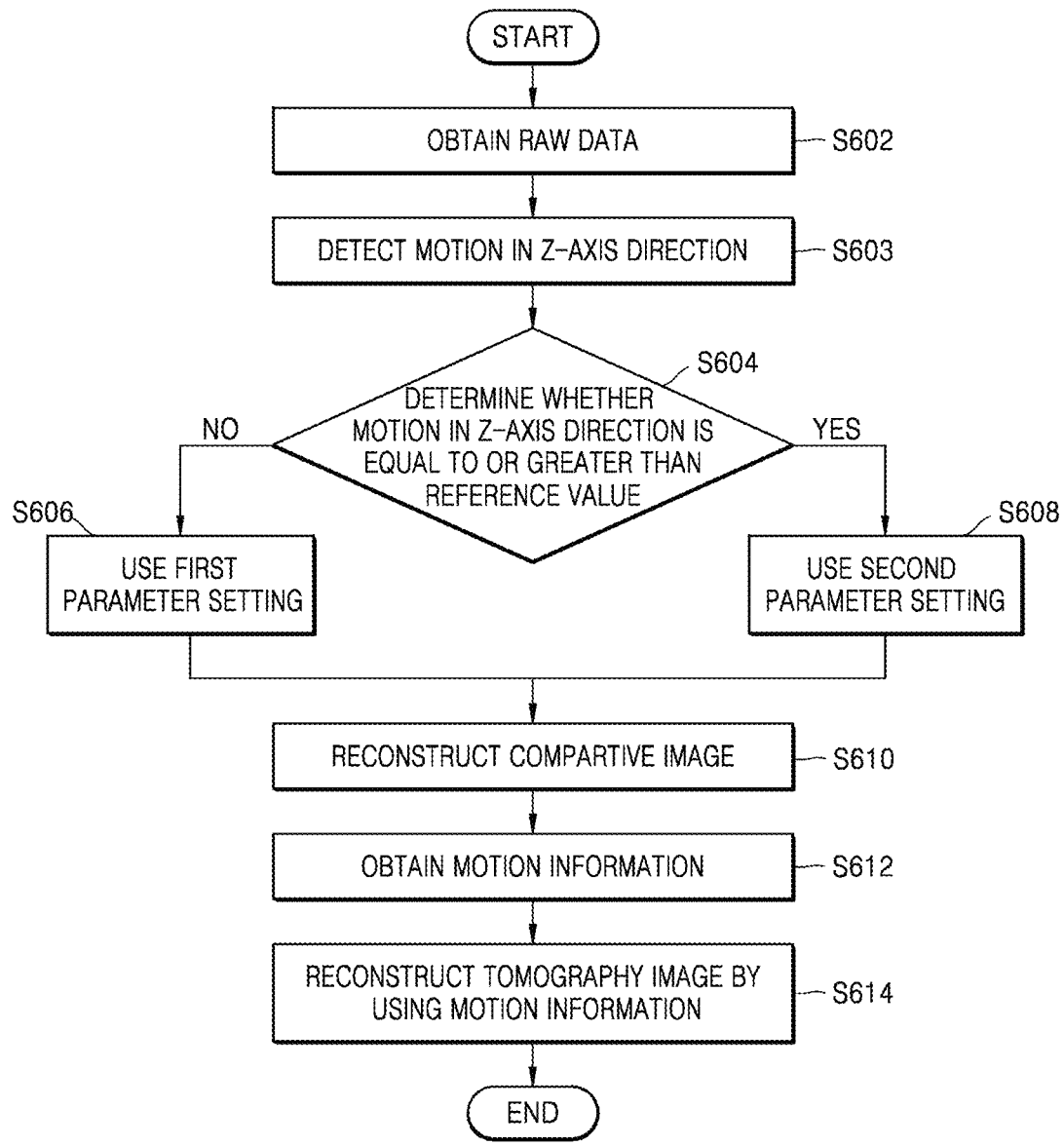

FIG. 12

| TYPE OF PROTOCOL | MOTION CORRECTION PARAMETERS |
|---|---|
| LUNG | SECOND PARAMETER |
| HEART | FIRST PARAMETER |
| ABDOMEN | SECOND PARAMETER |
|  |  |

FIG. 13

```
         START
           ↓
   OBTAIN RAW DATA                              — S1302
           ↓
   SEGMENT RAW DATA OR
   RECONSTRUCTED IMAGE                          — S1304
           ↓
   DETERMINE MOTION CORRECTION
   PARAMETERS ACCORDING TO REGIONS              — S1306
           ↓
   RECONSTRUCT COMPARATIVE IMAGE                — S1308
           ↓
   OBTAIN MOTION INFORMATION                    — S1310
           ↓
   RECONSTRUCT TOMOGRAPHY IMAGE
   BY USING MOTION INFORMATION                  — S1312
           ↓
          END
```

METHOD AND APPARATUS FOR PROCESSING MEDICAL IMAGE

CROSS-REFERENCE TO RELATED APPLICATION

This application is related to and claims priority to Korean Patent Application No. 10-2016-0133075, filed on Oct. 13, 2016, the disclosure of which is incorporated herein in its entirety by reference.

TECHNICAL FIELD

The present disclosure relates to a method and apparatus for processing a medical image and a computer-readable recording medium having recorded thereon computer program code for executing the method.

BACKGROUND

Medical imaging apparatuses are used to obtain images of internal structures of objects. Medical imaging apparatuses that are non-invasive testing apparatuses capture and process images of structural details, internal tissues, and the flow of fluids in human bodies and provide the images to users. The users, who are, for example, medical doctors, may diagnose health states and diseases of patients by using medical images output from the medical imaging apparatuses.

Examples of an apparatus for imaging an object by projecting X-rays toward a patient include a computed tomography (CT) apparatus.

A CT apparatus that is a medical imaging apparatus or a tomography apparatus may provide a cross-sectional image of an object and may clearly show internal structures (e.g., organs such as kidneys and lungs) of the object without overlapping them, unlike a general X-ray apparatus, and thus is widely used to accurately diagnose a disease.

However, when a tomography apparatus captures an image of an object that moves, a state of the object changes as time passes, and thus it is difficult to obtain a tomography image at a desired time or in a desired phase. For example, when a tomography scan is performed on a heart, in order to reconstruct a tomography image in a target phase, an electrocardiogram (ECG) of a patient is continuously monitored and imaging is performed at a time corresponding to the target phase. Since complicated processes for monitoring an ECG and setting an accurate imaging time have to be performed, complexity in system control is increased.

SUMMARY

To address the above-discussed deficiencies, it is a primary object to provide methods and apparatuses for reducing motion artifacts in medical images.

Also, objectives of embodiments improve motion correction performance by differently setting parameters used for motion correction according to motion characteristics of objects.

According to certain embodiments, an apparatus for processing a medical image includes: a data obtainer configured to obtain raw data generated by imaging an object; and a processor configured to determine motion correction parameters used to reconstruct an image to be used to obtain motion information, based on motion characteristics of the object, obtain the motion information by using the image reconstructed based on the determined motion correction parameters, and reconstruct a tomography image from the raw data by using the motion information.

The motion correction parameters include at least one from among an angular section and a time interval (such as a time interval duration duration) of raw data to be used to construct the image to be used to obtain the motion information.

The processor can be further configured to determine the motion characteristics of the object based on at least one from among the raw data and a type of a protocol performed when the object is imaged.

The motion characteristics of the object include a main motion direction of the object.

The processor can be further configured to measure the main motion direction of the object by comparing at least two pieces of projection data of different viewpoints.

The motion correction parameters include a first parameter setting for reconstructing an image by using raw data of an angular section greater than 0° and less than 180° and a second parameter setting for reconstructing an image by using raw data of an angular section equal to or greater than 180° and equal to or less than 360°.

The processor can be further configured to use the first parameter setting when a protocol performed when the object is imaged is a protocol for imaging a heart, and use the second parameter setting when the protocol used when the object is imaged is a protocol for imaging a lung or an abdomen.

The processor can be further configured to measure a motion of the object based on the raw data, and use the first parameter setting when a magnitude or a speed of the motion is less than a reference value and use the second parameter setting when the magnitude or the speed of the motion is equal to or greater than the reference value.

The processor can be further configured to use at least one pair of comparative images having an angle difference of 180° therebetween when the first parameter setting is used and use at least two comparative images having an angle difference greater than 0° and less than 360° therebetween when the second parameter setting is used.

A target phase can be located between phases of the at least two comparative images.

The processor can be further configured to segment the raw data or an image obtained by reconstructing the raw data and determine the motion correction parameters according to regions based on a segmentation result.

According to an aspect of another embodiment, a method of processing a medical image includes: obtaining raw data generated by imaging an object; determining motion correction parameters used to reconstruct an image to be used to obtain motion information, based on motion characteristics of the object; obtaining the motion information by using the image reconstructed based on the determined motion correction parameters; and reconstructing a tomography image from the raw data by using the motion information.

According to an aspect of another embodiment, a computer-readable recording medium has embodied thereon a computer program for executing a method of processing a medical image, when being read and performed by a processor, wherein the method includes: obtaining raw data generated by imaging an object; determining motion correction parameters used to reconstruct an image to be used to obtain motion information based on motion characteristics of the object; obtaining the motion information by using the image reconstructed based on the determined motion correction parameters; and reconstructing a tomography image from the raw data by using the motion information.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIG. 6 is a flowchart of a method of processing a medical image, according to an embodiment of the present disclosure;

FIG. 12 illustrates motion correction parameters according to a pre-determined protocol, according to an embodiment of the present disclosure;

FIG. 13 is a flowchart of a method of processing a medical image, according to an embodiment of the present disclosure;

DETAILED DESCRIPTION

Figure 1:
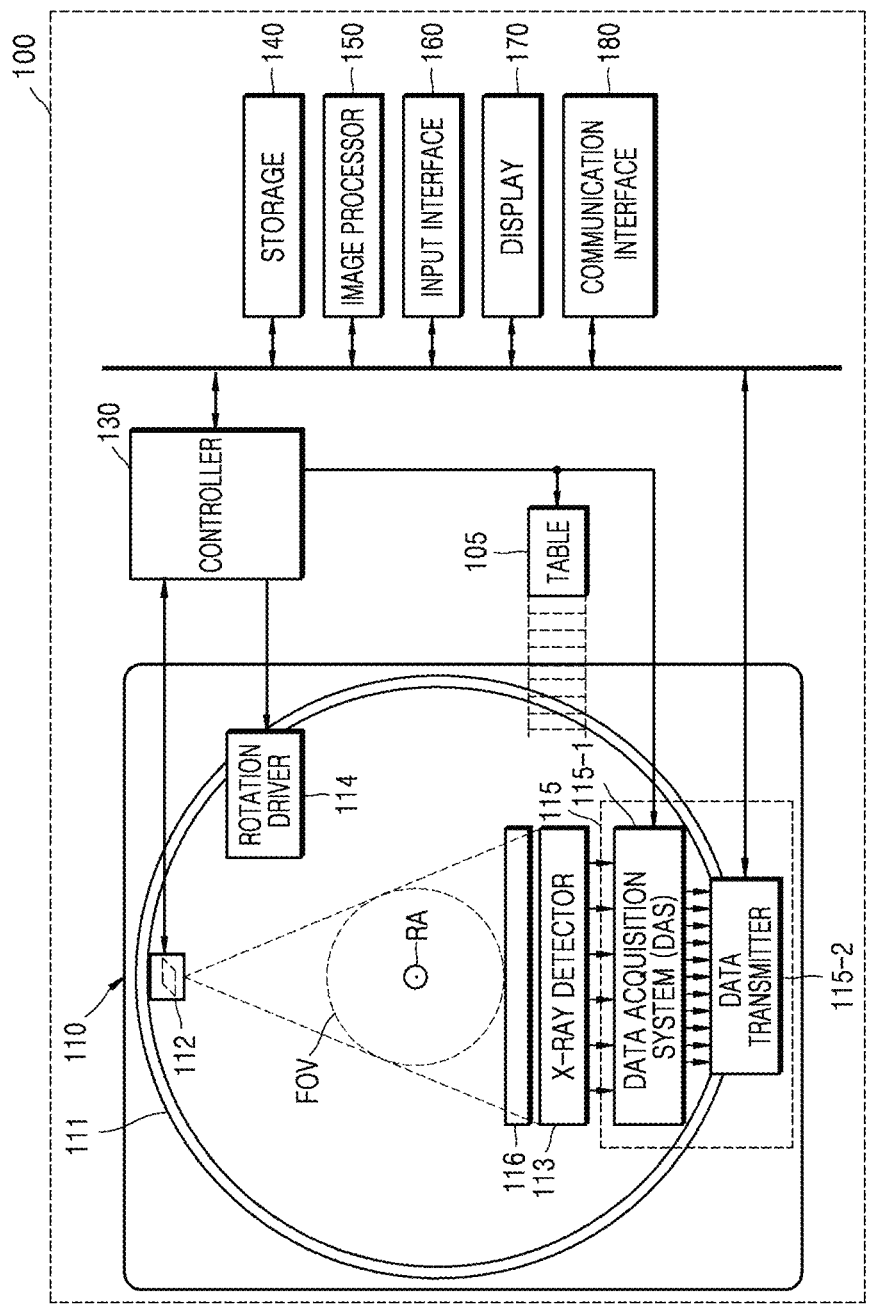
FIG. 1 illustrates a structure of a computed tomography (CT) system according to an embodiment of the present disclosure.

FIGS. 1 through 15, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

The principle of the present invention is explained and embodiments are disclosed so that the scope of the present invention is clarified and one of ordinary skill in the art to which the present invention pertains implements the present invention. The disclosed embodiments may have various forms.

Throughout the specification, like reference numerals or characters refer to like elements. In the present specification, all elements of embodiments are not explained, but general matters in the technical field of the present invention or redundant matters between embodiments will not be described. Terms 'part' and 'portion' used herein may be implemented using software or hardware, and, according to embodiments, a plurality of 'parts' or 'portions' may be implemented using a single unit or element, or a single 'part' or 'portion' may be implemented using a plurality of units or elements. The operational principle of the present invention and embodiments thereof will now be described more fully with reference to the accompanying drawings.

In the present specification, an image may include a medical image obtained by a medical imaging apparatus, such as a computed tomography (CT) apparatus, a magnetic resonance imaging (MRI) apparatus, an ultrasound imaging apparatus, or an X-ray apparatus.

Throughout the specification, the term 'object' is a thing to be imaged, and may include a human, an animal, or a part of a human or animal. For example, the object may include a part of a body (i.e., an organ), a phantom, or the like.

In the present specification, a 'CT system' or 'CT apparatus' refers to a system or apparatus configured to emit X-rays while rotating around at least one axis relative to an object and photograph the object by detecting the X-rays.

In the specification, a 'CT image' refers to an image constructed from raw data obtained by photographing an object by detecting X-rays that are emitted as the CT system or apparatus rotates about at least one axis with respect to the object.

Expressions such as "at least one of", when preceding a list of elements, modify the entire list of elements and do not modify the individual elements of the list.

FIG. 1 illustrates a structure of a CT system 100 according to an embodiment.

The CT system 100 may include a gantry 110, a table 105, a controller 130, a storage 140, an image processor 150, an input interface 160, a display 170, and a communication interface 180.

The gantry 110 may include a rotating frame 111, an X-ray generator 112, an X-ray detector 113, a rotation driver 114, and a readout device 115.

The rotating frame 111 may receive a driving signal from the rotation driver 114 and rotate around a rotation axis (RA).

An anti-scatter grid 116 may be disposed between an object and the X-ray detector 113 and may transmit most of primary radiation and attenuate scattered radiation. The object may be positioned on the table 105 which may move, tilt, or rotate during a CT scan.

The X-ray generator 112 receives a voltage and a current from a high voltage generator (HVG) to generate and emit X-rays.

The CT system 100 may be implemented as a single-source CT system including one X-ray generator 112 and one X-ray detector 113, or as a dual-source CT system including two X-ray generators 112 and two X-ray detectors 113.

The X-ray detector 113 detects radiation that has passed through the object. For example, the X-ray detector 113 may detect radiation by using a scintillator, a photon counting detector, etc.

Methods of driving the X-ray generator 112 and the X-ray detector 113 may vary depending on scan modes used for scanning of the object. The scan modes are classified into an axial scan mode and a helical scan mode, according to a path along which the X-ray detector 113 moves. Furthermore, the scan modes are classified into a prospective mode and a retrospective mode, according to a time interval during which X-rays are emitted.

The controller 130 may control an operation of each of the components of the CT system 100. The controller 130 may include a memory configured to store program codes for performing a function or data and a processor configured to process the program codes or the data. The controller 130 may be implemented in various combinations of at least one memory and at least one processor. The processor may generate or delete a program module according to an operating status of the CT system 100 and process operations of the program module.

The readout device 115 receives a detection signal generated by the X-ray detector 113 and outputs the detection signal to the image processor 150. The readout device 115 may include a data acquisition system (DAS) 115-1 and a data transmitter 115-2. The DAS 115-1 uses at least one amplifying circuit to amplify a signal output from the X-ray detector 113, and outputs the amplified signal. The data transmitter 115-2 uses a circuit such as a multiplexer (MUX) to output the signal amplified in the DAS 115-1 to the image processor 150. According to a slice thickness or a number of slices, only some of a plurality of pieces of data collected by the X-ray detector 113 may be provided to the image processor 150, or the image processor 150 may select only some of the plurality of pieces of data.

The image processor 150 obtains tomography data from a signal obtained by the readout device 115 (e.g., pure data that is data before being processed). The image processor 150 may pre-process the obtained signal, convert the obtained signal into tomography data, and post-process the tomography data. The image processor 150 may perform some or all of the processes described herein, and the type or order of processes performed by the image processor 150 may vary according to embodiments.

The image processor 150 may perform pre-processing, such as a process of correcting sensitivity irregularity between channels, a process of correcting a rapid decrease of signal strength, or a process of correcting signal loss due to an X-ray absorbing material, on the signal obtained by the readout device 115.

According to embodiments, the image processor 150 may perform some or all of the processes for reconstructing a tomography image, to thereby generate the tomography data. According to an embodiment, the tomography data may be in the form of data that has undergone back-projection, or in the form of a tomography image. According to embodiments, additional processing may be performed on the tomography data by an external device such as a server, a medical apparatus, or a portable device.

Raw data is a set of data values corresponding to intensities of X-rays that have passed through the object, and may include projection data or a sinogram. The data that has undergone back-projection is obtained by performing back-projection on the raw data by using information about an angle at which X-rays are emitted. The tomography image is obtained by using image reconstruction techniques including back-projection of the raw data.

The storage 140 is a storage medium for storing control-related data, image data, etc., and may include a volatile or non-volatile storage medium.

The input interface 160 receives control signals, data, etc., from a user. The display 170 may display information indicating an operational status of the CT system 100, medical information, medical image data, etc.

The CT system 100 includes the communication interface 180 and may be connected to external devices, such as a server, a medical apparatus, and a portable device (smartphone, tablet personal computer (PC), wearable device, etc.), via the communication interface 180.

The communication interface 180 may include one or more components that enable communication with an external device. For example, the communication interface 180 may include a short distance communication module, a wired communication module, and a wireless communication module.

The communication interface 180 may receive control signals and data from an external device and transmit the received control signals to the controller 130 so that the controller 130 may control the CT system 100 according to the received control signals.

Alternatively, by transmitting a control signal to an external device via the communication interface 180, the controller 130 may control the external device according to the control signal.

For example, the external device may process data according to a control signal received from the controller 130 via the communication interface 180.

A program for controlling the CT system 100 may be installed on the external device and may include instructions for performing some or all of the operations of the controller 130.

The program may be preinstalled on the external device, or a user of the external device may download the program from a server that provides an application for installation. The server that provides an application may include a recording medium having the program recorded thereon.

According to embodiments, the CT system 100 may or may not use contrast media during a CT scan, and may be implemented as a device connected to other equipment.

Figure 2:
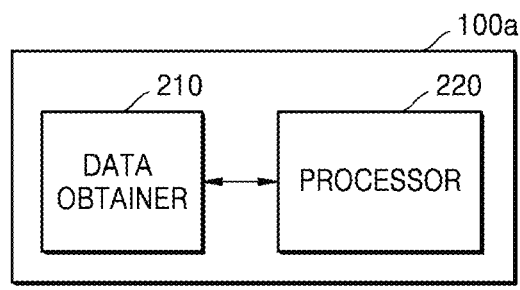
FIG. 2 illustrates a structure of an apparatus for processing a medical image, according to an embodiment of the present disclosure.

FIG. 2 illustrates a structure of an apparatus 100a for processing a medical image, according to an embodiment.

A motion of a patient during a CT scan causes motion artifacts to occur in a final reconstructed image, resulting in deterioration in image quality. To prevent motion artifacts, a method that asks the patient to hold his/her breath during a CT scan of the chest or abdomen may be used. If the patient fails to hold his/her breath, image quality is deteriorated, thereby making diagnosis difficult. In particular, since high-end equipment, for example, equipment used for cardiac imaging, is not always used for thoracic-abdominal imaging, a scan speed may not be high and the patient may have to hold his/her breath for a long time. Also, patients with abnormal lungs or older patients or infants may fail to hold their breath for more than 10 seconds during which imaging is performed. An objective of an apparatus for processing a medical image according to embodiments is to effectively remove motion artifacts occurring due to the breathing of a patient or a motion in the body.

The apparatus 100a according to an embodiment includes a data obtainer 210 and a processor 220.

The apparatus 100a may be implemented in the form of a CT system, a general-purpose computer, a portable terminal, or a kiosk. The portable terminal may be implemented in the form of, for example, a smart phone, a tablet PC, or the like.

The data obtainer 210 is a system, device or circuit that obtains raw data that is generated by imaging an object. The raw data may correspond to projection data or a sinogram. According to an embodiment, the raw data is raw data obtained by a helical scan in a CT system.

According to an embodiment, the data obtaining unit 210 can be a scanner that obtains the raw data by imaging the object by using X-rays. The scanner may include, for example, the X-ray generator 112 and the X-ray detector 113. According to the present embodiment, the data obtainer 210 obtains the raw data by imaging the object with a protocol that is set under the control of the processor 220.

According to an embodiment, the data obtainer 210 can be a communication interface that obtains the raw data from an external device. The external device includes, for example, a CT system, a medical data server, a terminal of another user, or the like. According to the present embodiment, the data obtainer 210 is connected to the external device through any of various wired or wireless networks, such as, a wired cable, a local area network (LAN), a mobile communication network, or the Internet.

The processor 220 is able to control an overall operation of the apparatus 100a and process data. The processor 220 may include one or more processors. According to an embodiment, the processor 220 that performs both operations of controlling a scanner and processing the raw data may be implemented as one or a plurality of processors. According to another embodiment, the processor 220 may be at least one processor that processes the raw data received from the external device.

The processor 220 determines motion correction parameters used to reconstruct an image to be used to obtain motion information based on motion characteristics of the object, obtains the motion information by using the image reconstructed based on the determined motion correction parameters, and reconstructs a tomography image from the raw data by using the motion information. The motion characteristics of the object can include one or more of: a motion direction of the object, a motion magnitude of the object, or motion characteristics of a region of interest of the object.

According to an embodiment, the processor 220 obtains the motion characteristics of the object by using the raw data, data obtained by performing predetermined processing on the raw data, or data reconstructed from the raw data. For example, the processor 220 is able to compare two pieces of projection data having an angle difference of 180° to obtain the motion characteristics of the object. According to an embodiment, a motion direction and a motion magnitude of the object represent a motion magnitude or a motion speed along each of the X, Y, and Z-axes. Here, the Z-axis refers to an axis perpendicular to a plane in which the X-ray generator 112 rotates. According to an embodiment, the motion characteristics of the object correspond to a motion magnitude in a Z-axis direction.

According to another embodiment, the motion characteristics of the object are determined according to a type of a protocol performed when the object is imaged. For example, when the object is imaged and a cardiac imaging protocol is used, the motion characteristics of the object are defined as motion characteristics corresponding to the heart. The heart has a high motion speed along the X and Y-axes and a motion periodicity, and thus the motion characteristics of the heart may be defined according to these characteristics. Alternatively, when the object is imaged and an abdominal imaging protocol is used, the motion characteristics of the object are defined as motion characteristics corresponding to the abdomen. The abdomen has a large motion magnitude in the Z-axis direction due to the diaphragm and the diaphragm moves according to breathing characteristics, and thus the motion characteristics of the abdomen may be defined according to these characteristics.

The processor 220 reconstructs at least two images from the raw data to obtain the motion information. In the present specification, an image used to obtain the motion information is referred to as a comparative image. The motion correction parameters refer to parameters used to obtain the at least two comparative images. According to an embodiment, the motion correction parameters represent a size of an angular section of raw data used to obtain the motion information. For example, the motion correction parameters may include a first parameter setting for reconstructing an image by using raw data of two angular sections each having a size less than 180° with an angle difference of 180° therebetween, and a second parameter setting for reconstructing an image by using raw data of two intervals each having a size equal to or greater than 180° with a predetermined angle difference therebetween.

The processor 220 obtains the motion information by using the at least two comparative images reconstructed by using the motion correction parameters. The motion information may be, for example, a two-dimensional (2D) or three-dimensional (3D) motion vector field (MVF). The processor 220 can obtain the motion information by matching the at least two images.

When the motion information is obtained, the processor 220 reconstructs a tomography image by performing motion compensation in an image reconstruction process. The processor 220 is able to reconstruct the tomography image by performing filtered back projection on the raw data. In a reconstruction process, the processor 220 can perform the motion compensation by warping rays in a motion direction by using the motion information.

The motion information may represent a motion between at least two reference phases corresponding to the at least two comparative images. According to an embodiment, the processor 220 calculates target motion information between a reference phase and a target phase by using interpolation, and reconstructs the tomography image in the target phase by using the target motion information.

According to an embodiment, when the target phase is set, the processor 220 determines the motion correction parameters so that the target phase is located between phases of the at least two comparative images.

Figure 3:
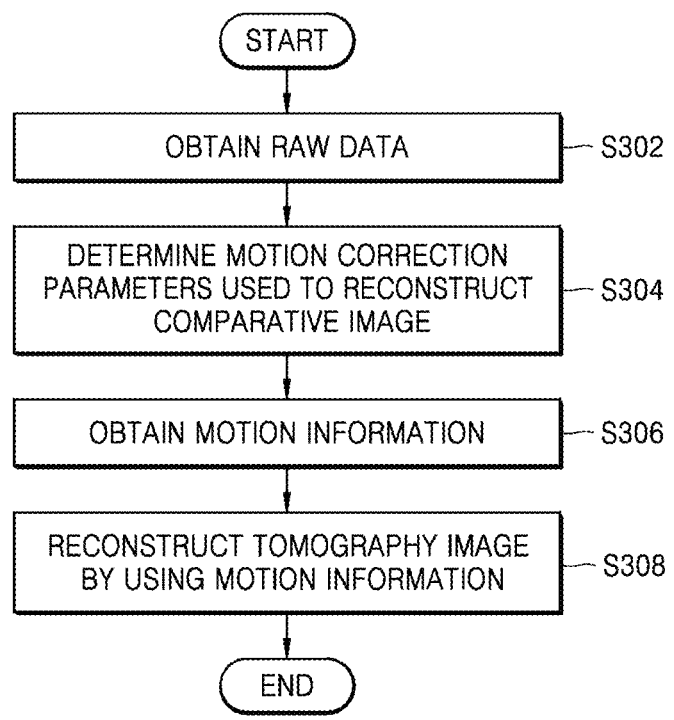
FIG. 3 is a flowchart of a method of processing a medical image, according to an embodiment of the present disclosure.

FIG. 3 is a flowchart of a method of processing a medical image, according to an embodiment.

Operations of the method according to embodiments may be performed by various electronic apparatuses including at least one processor. The following will be explained based on the assumption that the apparatus 100 or 100a performs the method. Therefore, the description given for the apparatus 100 or 100a may be applied to the method, and conversely, the description given for the method may be applied to the apparatus 100 or 100a. Although the method according to embodiments is performed by the apparatus 100 or 100a, embodiments are not limited thereto, and the method may be performed by various other electronic apparatuses.

In operation S302, an apparatus for processing a medical image (referred to as 'medical image processing apparatus') obtains raw data generated by imaging an object. The raw data may be obtained when the medical image processing apparatus that performs the method images the object, or may be obtained by receiving the raw data from an external device.

Next, in operation S304, the medical image processing apparatus determines motion correction parameters used to reconstruct at least two comparative images. Motion characteristics of the object may be determined based on, for example, the raw data, reconstructed images, and a type of a protocol. The motion correction parameters represent, for example, an angular section of raw data used to reconstruct the comparative images.

Next, in operation S306, the medical image processing apparatus obtains motion information by using the comparative images reconstructed by using the determined motion correction parameters. The medical image processing apparatus may obtain the motion information by, for example, matching the at least two comparative images. The motion information may be, for example, a 2D or 3D MVF.

Next, in operation S308, the medical image processing apparatus applies the motion information to a reconstruction process and reconstructs a motion compensated tomography image from the raw data. For example, in a tomography image reconstruction process, the medical image processing apparatus may perform motion compensation by warping rays based on the motion information.

Figure 4A:
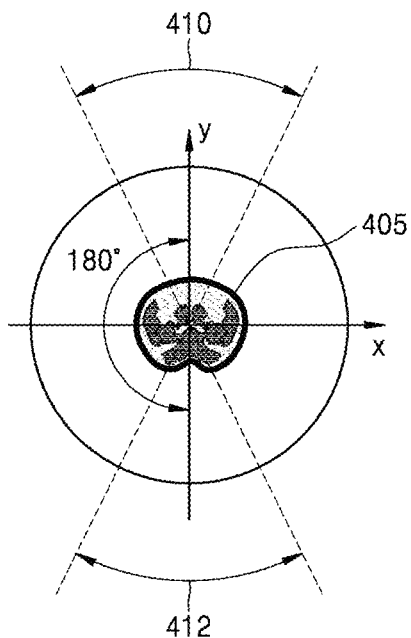
FIGS. 4A and 4B are views for explaining a process of obtaining motion correction parameters and a comparative image, according to an embodiment of the present disclosure.
Figure 4B:
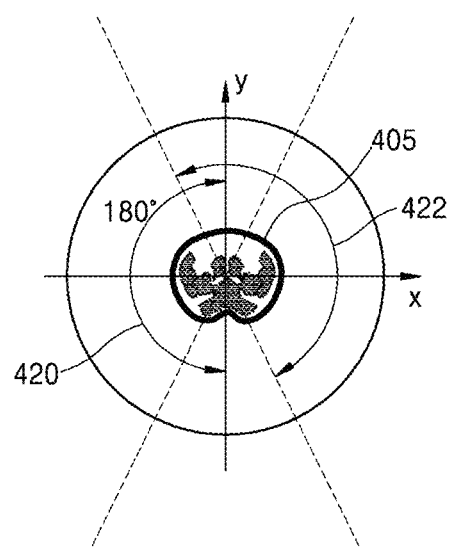

FIGS. 4A and 4B are views for explaining a process of obtaining motion correction parameters and a comparative image, according to an embodiment.

According to an embodiment, a helical scan is performed while an X-ray generator rotates around an object 405 and the object 405 moves in a Z-axis direction. The X-ray generator may emit X-rays in the form of a cone beam, and an X-ray detector is able to detect the X-rays passing through the object 405 to generate raw data. A medical image processing apparatus may generate the raw data by using a parallel beam generated by rebinning the cone beam.

The processor 220 generates a tomography image by reconstructing the raw data. The processor 220 is able to generate the tomography image from the raw data by using various reconstruction methods. For example, the processor 220 may reconstruct the tomography image by using a partial angle reconstruction (PAR) method that reconstructs a tomography image by using raw data of a section less than 180°, a half reconstruction method that reconstructs a tomography image by using raw data of a section of 180°+ additional angle, and a full reconstruction method that reconstructs a tomography image by using raw data of a section of 360°. According to an embodiment, the additional angle may be a fan angle that is a vertex angle of a fan-shaped cross-section of the X-ray cone-beam.

According to an embodiment, motion correction parameters represent a size of an angular section of raw data used to reconstruct a comparative image. For example, the processor 220 may use a PAR method, a half reconstruction method, or a full reconstruction method according to motion characteristics of the object. Since the PAR method uses raw data of a short angular section, the PAR method has small motion artifacts but has only edge information of the object in some directions. Since the half reconstruction method and the full reconstruction method use raw data of an angular section that is longer than that of the PAR method, the half reconstruction method and the full reconstruction method have edge information of the object in all directions but have a higher risk of motion artifacts than the PAR method.

According to an embodiment, the processor 220 uses a first comparative image and a second comparative image respectively obtained from raw data of two angular sections 410 and 412 equal to or greater than 0° and less than 180° by using a first parameter setting of the motion correction parameters. The first comparative image and the second comparative image may be partial angle reconstructed images. For example, the first comparative image may be generated from the raw data of the first angular section 410, and the second comparative image may be generated from the raw data of the second angular section 412. The first angular section 410 and the second angular section 412 have a conjugate relationship having an angle difference of 180° therebetween. According to the present embodiment, since a view in the first angular section 410 and a view in the second angular section 412 are the same, a surface of the object 405 detected when the object 405 is imaged in the first angular section 410 and a surface of the object 405 detected when the object 405 is imaged in the second angular section 412 are the same.

The processor 220 is able to use a third comparative image and a fourth comparative image obtained respectively from raw data of two angular sections 420 and 422 equal to or greater than 180° and equal to or less than 360° by using a second parameter setting of the motion correction parameters. The third comparative image and the fourth comparative image may be images reconstructed by using a half reconstruction method or a full reconstruction method. For example, the third comparative image may be generated from the raw data of the third angular section 420, and the fourth comparative image may be generated from the raw data of the fourth angular section 422. An angle difference between the third angular section 420 and the fourth angular section 422 may be arbitrarily determined.

Since the second parameter setting utilizes full edge information, the third comparative image and the fourth comparative image are not limited to an angle difference of 180° but may have an arbitrary angle difference. Therefore, not only a motion of 180° difference but also a motion of any of other angle differences may be detected, thereby improving motion correction performance. Also, when a time interval, for example a time interval duration, between two comparative images is short, the possibility of a linear motion is high and motion correction performance may be improved. Especially, when there is a large motion in the Z-axis direction such as an abdominal motion occurring due to breathing, the second parameter setting using the full edge information may improve motion correction performance.

Also, when the second parameter setting is used, comparative images may be obtained for two or more viewpoints, motion information at each time may be estimated, and a piecewise-linear motion may also be estimated. It is actually found that motion correction using a half reconstructed image, instead of obtaining a comparative image by using a PAR method from a reconstructed image of a patient who has undergone breathing during abdominal imaging, is more effective when there is a large motion in the Z-axis direction.

Figure 5A:
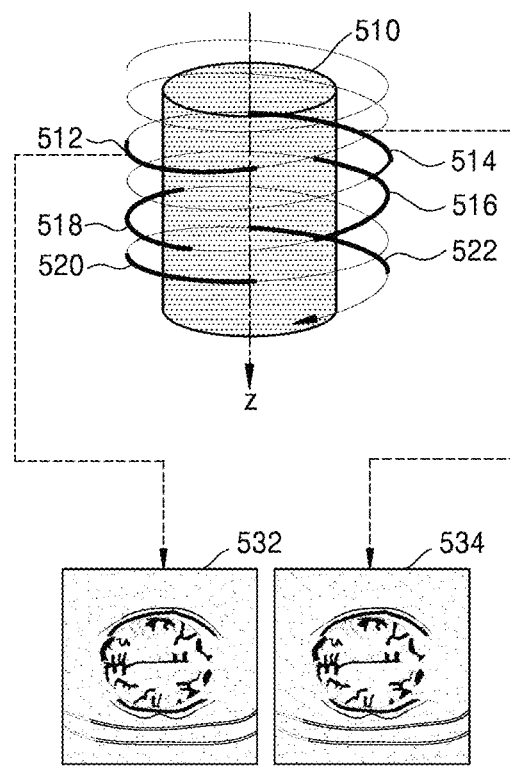
FIGS. 5A and 5B are views for explaining a process of imaging an object by using a first parameter setting, according to an embodiment of the present disclosure.
Figure 5B:
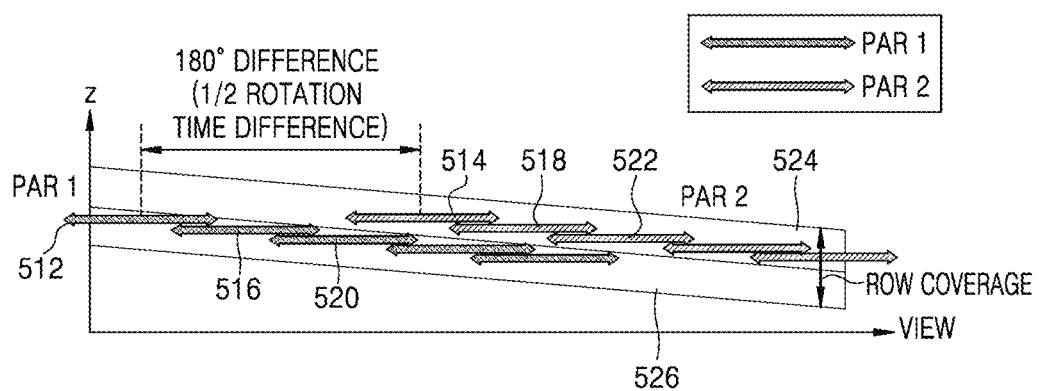
Figure 5C:
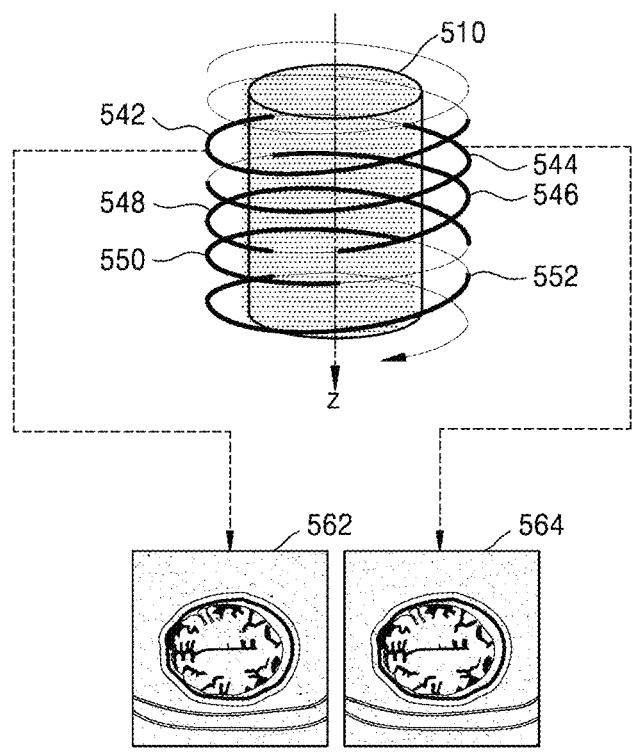
FIGS. 5C and 5D are views for explaining a process of imaging an object by using a second parameter setting, according to an embodiment of the present disclosure.
Figure 5D:
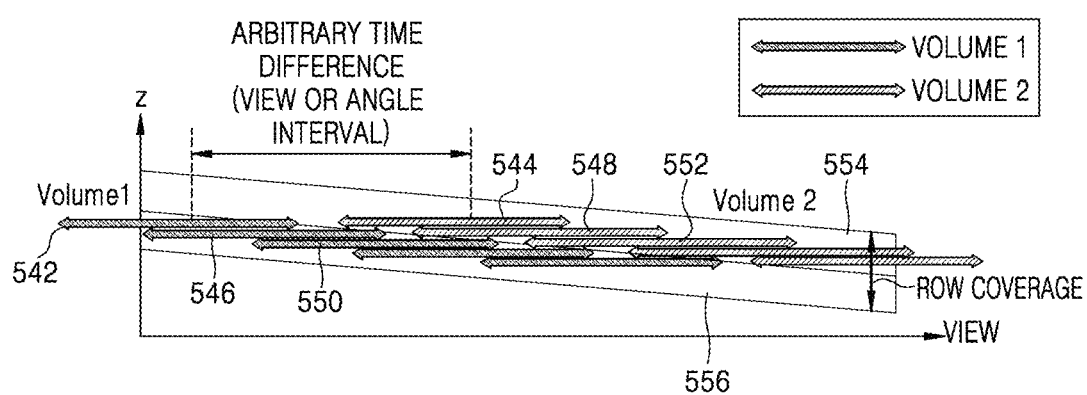

FIGS. 5A and 5B are views for explaining a process of imaging an object by using a first parameter setting, according to an embodiment. FIGS. 5C and 5D are views for explaining a process of imaging an object by using a second parameter setting, according to an embodiment.

Angular sections denoted by 512, 514, 516, 518, 520, and 522 in FIG. 5A are denoted by the same reference numerals in FIG. 5B. An arrow range indicating each angular section in FIG. 5B represents a reconstruction coverage in consideration of a field of view (FOV). Also, a section between reference lines 524 and 526 represents a row coverage, which is a Z-axis range coverable at each position of an X-ray detector.

According to an embodiment, a helical scan is performed while an X-ray generator rotates around an object 510. When the object 510 is imaged by using a first parameter setting, as shown in FIG. 5A, the processor 220 generates partial angle reconstructed images by using raw data of the angular sections 512, 514, 516, 518, 520, and 522 less than 180° and uses the partial angle reconstructed images as comparative images. The processor 220 is able to generate two comparative images by using raw data of two angular sections within one period. For example, the processor 220 may reconstruct a first comparative image 532 from the raw data of the angular section 512 and may reconstruct a second comparative image 534 from the raw data of the angular section 514. The first comparative image 532 and the second comparative image 534 may correspond to the same Z-axis position. Since the angular section 512 and the angular section 514 have different Z-axis positions but have a row converge that covers a common Z-axis position, the raw data of the angular section 512 and the angular section 514 have data about the same Z-axis position. Specifically, although the angular section 512 and the angular section 514 have a Z-axis position difference, since the Z-axis position difference between the angular section 512 and the angular section 514 is within a row coverage range, comparative images of the same z-axial position may be obtained. In addition, since the angular section 512 and the angular section 514 have a conjugate relationship, the angular section 512 and the angular section 514 have edge information in the same direction. Accordingly, the first comparative image 532 and the second comparative image 534 indicate edge information about the same Z-axis position, and the processor 220 may obtain motion information of the object 510 in X and Y-axis directions by comparing the first comparative image 532 and the second comparative image 534.

The processor 220 is able to generate two comparative images that are partial reconstructed images by selecting two angular sections having a row coverage including a target Z-axis position and a conjugate relationship. For example, the processor 220 may generate a first comparative image and a second comparative image from raw data of the angular section 516 and the angular section 518, or may generate a first comparative image and a second comparative image from raw data of the angular section 520 and the angular section 522. The processor 220 may also generate a first comparative image and a second comparative image of the target Z-axis position.

Angular sections denoted by 542, 544, 546, 548, 550, and 552 in FIG. 5C are denoted by the same reference numerals in FIG. 5D. An arrow range indicating each angular section in FIG. 5D represents a reconstruction coverage in consideration of an FOV. Also, a section between reference lines 554 and 556 represents a row coverage, which is a Z-axis range coverable at each position of the X-ray detector.

According to an embodiment, a helical scan is performed while the X-ray generator rotates around the object 510. When the object 510 is imaged by using a second parameter setting, as shown in FIG. 5C, the processor 220 generates half reconstructed images by using raw data of the angular sections 542, 544, 546, 548, 550, and 552 equal to or greater than 180° and uses the half reconstructed images as comparative images. The processor 220 is able to generate two comparative images by using raw data of two angular sections. For example, the processor 220 may reconstruct a first comparative image 562 from the raw data of the angular section 542 and may reconstruct a second comparative image 564 from the raw data of the angular section 544. The first comparative image 562 and the second comparative image 564 may correspond to the same Z-axis position. Since the angular section 542 and the angular section 544 have different Z-axis positions but have a row converge that covers a common Z-axis position, the raw data of the angular section 542 and the angular section 544 have data about the same Z-axis position. Specifically, although the angular section 542 and the angular section 544 have a Z-axis position difference, the Z-axis position difference between the angular section 542 and the angular section 544 is within a row coverage range, and thus, comparative images of the same Z-axis position may be obtained. In addition, since the first comparative image 562 and the second comparative image 564 have angular sections equal to or greater than 180°, the first comparative image 562 and the second comparative image 564 have edge information of a surface of the object 510 in all directions, that is, 360°. Accordingly, the first comparative image 562 and the second comparative image 564 indicate edge information about the same Z-axis position, and the processor 220 is able to obtain motion information of the object 510 in the X and Y-axis directions by comparing the first comparative image 562 and the second comparative image 564.

The processor 220 is able to generate two comparative images that are partial angle reconstructed images by selecting two angular sections having a row coverage including a target Z-axis position and a conjugate relationship. For example, the processor 220 may generate a first comparative image and a second comparative image from the raw data of the angular section 516 and the angular section 518, or may generate a first comparative image and a second comparative image from the raw data of the angular section 520 and the angular section 522. The processor 220 may also generate a first comparative image and a second comparative image of the target Z-axis position. According to the second parameter setting, an angle difference between angular sections for obtaining two comparative images may be arbitrarily determined, and the processor 220 may generate two comparative images from raw data of two angular sections having a row coverage including a target Z-axis position.

FIG. 6 is a flowchart of a method of processing a medical image, according to an embodiment.

The method according to the present embodiment uses a motion of an object in a Z-axis direction as motion characteristics of the object. According to the present embodiment, the method detects the motion of the object in the Z-axis direction from raw data or a reconstructed image, and determines motion correction parameters in accordance with the motion in the Z-axis direction.

First, in operation S602, a medical image processing apparatus obtains raw data generated by imaging an object. The raw data may be obtained when the medical image processing apparatus that performs the method images the object, or may be obtained by receiving the raw data from an external device.

Next, in operation S603, the medical image processing apparatus detects a motion of the object in a Z-axis direction from the raw data of the object or a reconstructed image generated by reconstructing the raw data. According to an embodiment, the medical image processing apparatus detects the motion of the object in the Z-axis direction by comparing two pieces of projection data having an angle difference of 180° therebetween.

Next, in operations S604, S606, and S608, the medical image processing apparatus determines motion correction parameters based on the motion of the object in the Z-axis direction. When it is determined in operation S604 that the motion in the Z-axis direction is equal to or larger than a reference value, the method proceeds to operation S608. In operation S608, the medical image processing apparatus uses a second parameter setting. When it is determined in operation S604 that the motion in the Z-axis direction is less than the reference value, the method proceeds to operation S606. In operation S606, the medical image processing apparatus uses a first parameter setting. Here, the first parameter setting is a setting in which an angular section used to reconstruct a comparative image is less than that of the second parameter setting. For example, the first parameter setting uses a partial angle reconstructed image as a comparative image, and the second parameter setting uses a half reconstructed image as a comparative image.

Next, in operation S610, the medical image processing apparatus reconstructs at least two comparative images by using the determined motion correction parameters.

Next, in operation S612, the medical image processing apparatus obtains motion information by using the comparative images reconstructed by using the determined motion correction parameters. The medical image processing apparatus is able to obtain the motion information by, for example, matching the at least two comparative images. The motion information may be, for example, a 2D or 3D MVF.

Next, in operation S614, the medical image processing apparatus applies the motion information to a reconstruction process, and reconstructs a motion compensated tomography image from the raw data. For example, in a tomography image reconstruction process, the medical image processing apparatus may perform motion compensation by warping rays based on the motion information.

Figure 7:
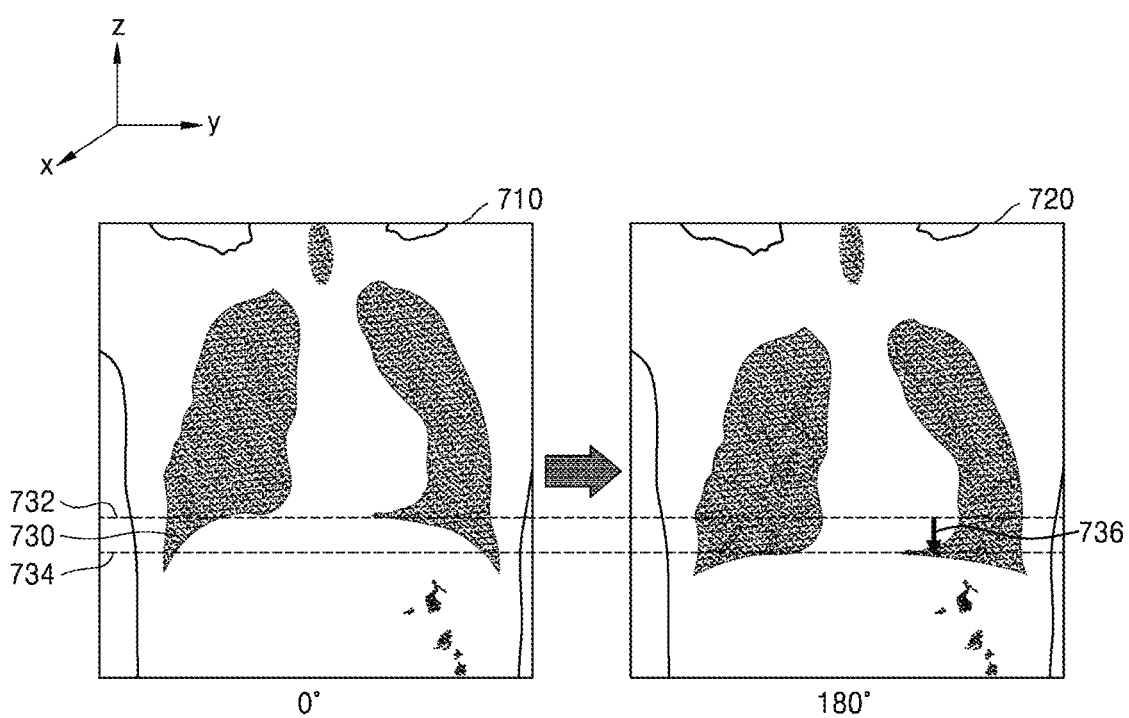
FIG. 7 is a view for explaining a process of detecting a motion of an object in a Z-axis direction, according to an embodiment of the present disclosure.

FIG. 7 is a view for explaining a process of detecting a motion of an object in a Z-axis direction, according to an embodiment.

When the abdomen of an object is imaged, a body part of the object has not only a motion in X and Y-axis directions, but also a motion in a Z-axis direction, due to breathing. For example, as shown in FIG. 7, when the abdomen is imaged, a diaphragm 730 moves up and down between a first position 732 and a second position 734 due to breathing. When a motion in the Z-axis direction occurs in this way, there is a limitation in compensating for the motion of the object in the Z-axis direction by using only edge information in some directions. According to the present embodiment, when the motion of the object in the Z-axis direction is detected to be equal to or larger than a reference value, the motion in the Z-axis direction is compensated for by using a second parameter setting that generates a comparative image from raw data of an angular section equal to or greater than 180°.

According to an embodiment, the medical image processing apparatus detects the motion in the Z-axis direction by using two pieces of projection data 710 and 720 having an angle difference of 180° therebetween. For example, the medical image processing apparatus may detect the motion in the Z-axis direction by compensating for a Z-axis position of each of the first projection data 710 and the second projection data 720 and matching the first projection data 710 and the second projection data 720. Alternatively, the medical image processing apparatus may reconstruct a half reconstructed image or a full reconstructed image from raw data, and may detect the motion in the Z-axis direction by using the reconstructed image. When the motion in the Z-axis direction occurs, the medical image processing apparatus may obtain motion information about the motion in the Z-axis direction by using a half reconstructed image or a full reconstructed image having edge information in all directions, and may compensate for the motion in the Z-axis direction in an image reconstruction process, thereby more effectively reducing motion artifacts.

Figure 8:
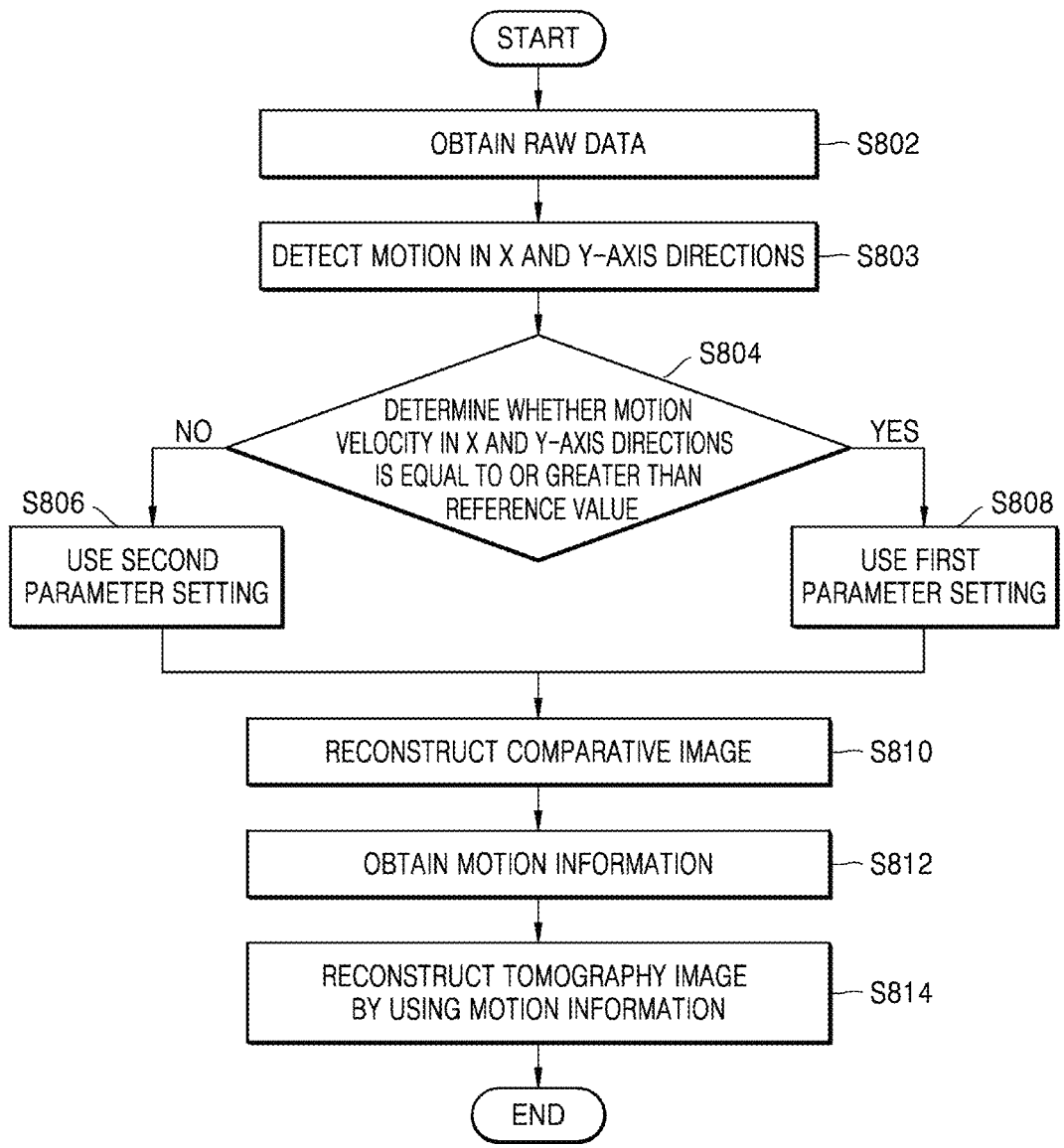
FIG. 8 is a flowchart of a method of processing a medical image, according to an embodiment of the present disclosure.

FIG. 8 is a flowchart of a method of processing a medical image, according to an embodiment.

The method according to the present embodiment uses a motion of an object in X and Y-axis directions as motion characteristics of the object. According to the present embodiment, the method detects a motion in the X and Y-axis directions of the object from raw data or a reconstructed image, and determines motion correction parameters in accordance with the motion in the X and Y-axis directions.

First, in operation S802, a medical image processing apparatus obtains raw data generated by imaging an object. The raw data may be obtained when the medical image processing apparatus that performs the method images the object, or may be obtained by receiving the raw data from an external device.

Next, in operation S803, the medical image processing apparatus detects a motion of the object in X and Y-axis directions from the raw data of the object or a reconstructed image generated by reconstructing the raw data. According to an embodiment, the medical image processing apparatus detects the motion of the object in the X and Y-axis directions by convoluting two pieces of projection data having an angle difference of 180° therebetween. Alternatively, the medical image processing apparatus may detect the motion in the X and Y-axis directions by using a reconstructed image reconstructed by using a half reconstruction or full reconstruction method.

Next, in operations S804, S806, and S808, the medical image processing apparatus determines motion correction parameters based on the motion of the object in the X and Y-axis directions. When it is determined in operation S804 that the motion in the X and Y-axis directions is equal to or greater than a reference value, the method proceeds to operation S808. In operation S808, the medical image processing apparatus uses a first parameter setting. When it is determined in operation S804 that the motion in the X and Y-axis direction is less than the reference value, the method proceeds to operation S806. In operation S806, the medical processing apparatus uses a second parameter setting. Here, the first parameter setting is a setting in which an angular section used to reconstruct a comparative image is less than that of the second parameter setting. For example, the first parameter setting uses a partial angle reconstructed image as a comparative image, and the second parameter setting uses a half reconstructed image as a comparative image.

Next, in operation S810, the medical image processing apparatus reconstructs at least two comparative images by using the determined motion correction parameters.

Next, in operation S812, the medical image processing apparatus obtains motion information by using the comparative images reconstructed by using the determined motion correction parameters. The medical image processing apparatus is able to obtain the motion information by, for example, matching the at least two comparative images. The motion information may be, for example, a 2D or 3D MVF.

Next, in operation S814, the medical image processing apparatus applies the motion information to a reconstruction process, and reconstructs a motion compensated tomography image from the raw data. For example, in a tomography image reconstruction process, the medical image processing apparatus may perform motion compensation by warping rays based on the motion information.

The medical image processing apparatus according to the present embodiment generates a comparative image having a high temporal resolution by using raw data of a short time interval (duration) and obtains motion information, when a magnitude or a speed of a motion in X and Y directions is equal to or greater than a reference value. For example, when the heart is imaged, a motion is fast and complex, and thus a high temporal resolution is required. According to the present embodiment, since motion information is obtained by using a comparative image, which is a partial angle reconstructed image, when the heart is imaged, the motion information and the comparative image having a high temporal resolution may be obtained even when information displayed in the comparative image is incomplete.

Figure 9:
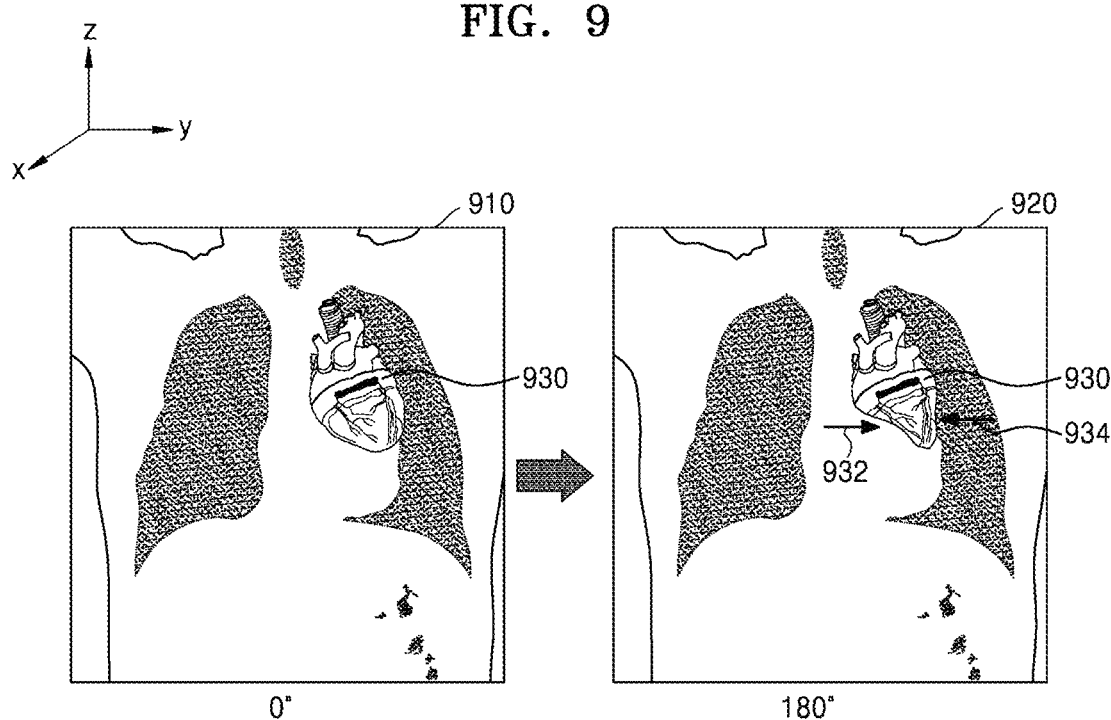
FIG. 9 illustrates raw data obtained by imaging an object, according to an embodiment of the present disclosure.

FIG. 9 illustrates raw data obtained by imaging an object, according to an embodiment.

An image 910 and an image 920 are projection data obtained by imaging a region including the heart 930. According to the present embodiment, when the heart 930 is imaged, a motion in a Z-axis direction is relatively small whereas a magnitude and a speed of motions 932 and 934 in X and Y-axis directions are relatively large. According to the present embodiment, since motion information is obtained by using a partial angle reconstructed image, motion information of an object having a fast and complex motion may be obtained at a high temporal resolution, thereby reducing motion artifacts.

Figure 10:
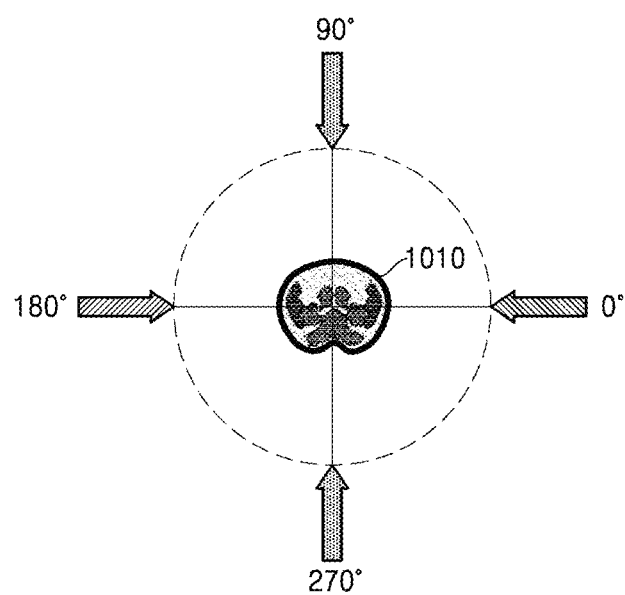
FIG. 10 is a view for explaining a method of imaging a comparative image, according to an embodiment of the present disclosure.

FIG. 10 is a view for explaining a method of imaging a comparative image, according to an embodiment.

According to an embodiment, when a motion of an object in X and Y directions is large, motion information may be obtained by generating comparative images in a first angular section and a second angular section having a conjugate relationship and motion information may be obtained by generating comparative images in a third angular section and a fourth angular section respectively having an angle difference of 90° from the first angular section and the second angular section. In this case, the comparative images are partial angle reconstructed images reconstructed from raw data of angular sections less than 180°. For example, as shown in FIG. 10, when an object 1010 is imaged, a medical image processing apparatus obtains first motion information from a first comparative image corresponding to 0° and a second comparative image corresponding to 180°, and obtains second motion information from a third comparative image corresponding to 90° and a fourth comparative image corresponding to 270°. In addition, the medical image processing apparatus may obtain final motion information from the first motion information and the second motion information.

A partial angle reconstructed image does not have edge information in all directions and has only edge information in some directions. The medical image processing apparatus according to the present embodiment is able to obtain motion information in all or almost all directions by obtaining two sets of motion information by using two pairs of comparative images corresponding to angular sections perpendicular to each other. According to an embodiment, all of the first comparative image, the second comparative image, the third comparative image, and the fourth comparative image may be images reconstructed from raw data having a row coverage including a predetermined Z position.

Figure 11:
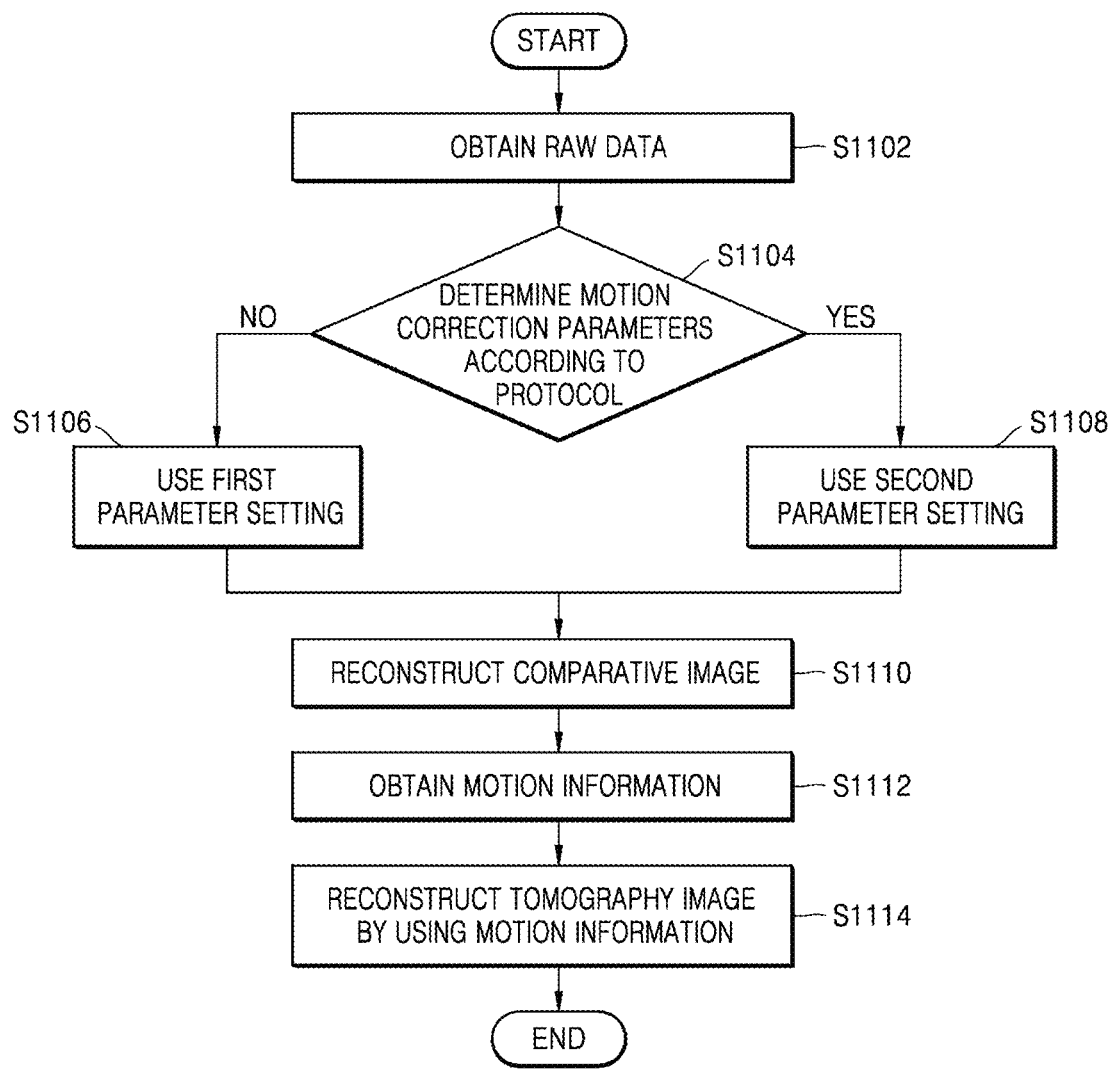
FIG. 11 is a flowchart of a method of processing a medical image, according to an embodiment of the present disclosure.

FIG. 11 is a flowchart of a method of processing a medical image, according to an embodiment.

The method according to the present embodiment determines motion characteristics of an object from a type of a protocol used when the object is imaged.

First, in operation S1102, a medical image processing apparatus obtains raw data generated by imaging an object. The raw data may be obtained when the medical image processing apparatus that performs the method images the object, or may be obtained by receiving the raw data from an external device.

Next, in operations S1104, S1106, and S1108, the medical image processing apparatus determines motion correction parameters based on a type of a protocol used when the object is imaged. The medical image processing apparatus uses a first parameter setting (S1106) or a second parameter setting (S1108) according to a pre-determined rule. Here, the first parameter setting is a setting in which an angular section used to reconstruct a comparative image is less than that of the second parameter setting. For example, the first parameter setting uses a partial angle reconstructed image as a comparative image, and the second parameter setting uses a half reconstructed image as a comparative image.

Next, in operation S1110, the medical image processing apparatus reconstructs at least two comparative images by using the determined motion correction parameters.

Next, in operation S1112, the medical image processing apparatus obtains motion information by using the comparative images reconstructed by using the determined motion correction parameters.

Next, in operation S1114, the medical image processing apparatus applies the motion information to a reconstruction process, and reconstructs a motion compensated tomography image from the raw data. For example, in a tomography image reconstruction process, the medical image processing apparatus may perform motion compensation by warping rays based on the motion information.

The medical image processing apparatus uses a protocol that is an imaging method set in advance according to the object. For example, the medical image processing apparatus uses a protocol that performs a helical scan of a path having a narrow interval at a low pitch when imaging a region with a fast motion (e.g., the heart) and uses a protocol that performs a helical scan of a path having a wide interval at a high pitch (e.g., 0.5 or more) when imaging a wide region whose motion is relatively small (e.g., the chest/the abdomen). That is, a protocol may reflect motion characteristics of the object, and in the present embodiment, the motion characteristics of the object are determined according to the protocol to determine the motion correction parameters. However, when scanning is performed at a high pitch, an edge direction varies according to a Z-axis slice. In this case, if a large motion in a Z-axis direction, such as breathing, occurs, motion estimation may not be performed between slices having different edge directions, thereby reducing the accuracy of the motion estimation. When all partial angle reconstructed images are arranged at 180° intervals as comparative images, since the images have the same edge direction irrespective of a Z-axis position, a decrease in the accuracy of motion estimation in an edge direction may be prevented. However, when a pitch is high, since the partial angle reconstructed images may not be reconstructed for all slices at 180° intervals, it is difficult to perform precise motion correction.

When the medical image processing apparatus includes a scanner, information about the protocol may be obtained from the medical imaging processing apparatus. In another embodiment, when the medical image processing apparatus receives the raw data from an external device, the medical image processing apparatus may receive the information about the protocol from the external device or obtain the information from information embedded in the raw data.

FIG. 12 illustrates motion correction parameters according to a pre-determined protocol, according to an embodiment.

According to an embodiment, motion correction parameters may be preset according to a protocol in the form of a look-up table as shown in FIG. 12. In another embodiment, the motion correction parameters according to the protocol may be set by a user.

FIG. 13 is a flowchart of a method of processing a medical image, according to an embodiment.

The method according to the present embodiment is able to use different motion correction parameters according to Z-axis sections when a tomography image is reconstructed by using the same raw data. When a region of an object and motion characteristics vary according to the Z-axis sections, motion artifacts may be more effectively reduced by using different motion correction parameters according to the Z-axis sections.

First, in operation S1302, a medical image processing apparatus obtains raw data generated by imaging an object. The raw data may be obtained when the medical image processing apparatus that performs the method images the object, or may be obtained by receiving the raw data from an external device.

Next, in operation S1304, the medical image processing apparatus performs segmentation by using the raw data of the object or a reconstructed image generated by reconstructing the raw data. For example, the medical image processing apparatus may perform segmentation by recognizing each body part from the raw data or the reconstructed image by using image matching or object recognition.

Next, in operation S1306, the medical image processing apparatus determines motion correction parameters based on a segmentation result. By using motion correction parameters that are preset for each body part, the medical image processing apparatus may apply the preset motion correction parameters to a Z-axis section corresponding to each body part. For example, the medical image processing apparatus may use a first parameter setting for a Z-axis section corresponding to the heart and a second parameter setting for a Z-axis section corresponding to the abdomen other than the heart. According to an embodiment, when the motion correction parameters are used differently according to the Z-axis sections, an angle difference between comparative images in the first parameter setting is set to 180°, and an angle difference between comparative images in the second parameter setting is set to 180°. The second parameter setting may have an arbitrary angle difference between the comparative images, but when the motion correction parameters are set differently according to Z-axis sections, an angle difference between the comparative images in the second parameter setting is set to be the same as an angle difference between the comparative images in the first parameter setting.

Next, in operation S1308, the medical image processing apparatus reconstructs at least two comparative images by using the determined motion correction parameters.

Next, in operation S1310, the medical image processing apparatus obtains motion information by using the comparative images reconstructed by using the determined motion correction parameters.

Next, in operation S1312, the medical image processing apparatus applies the motion information to a reconstruction process, and reconstructs a motion compensated tomography image from the raw data.

Figure 14:
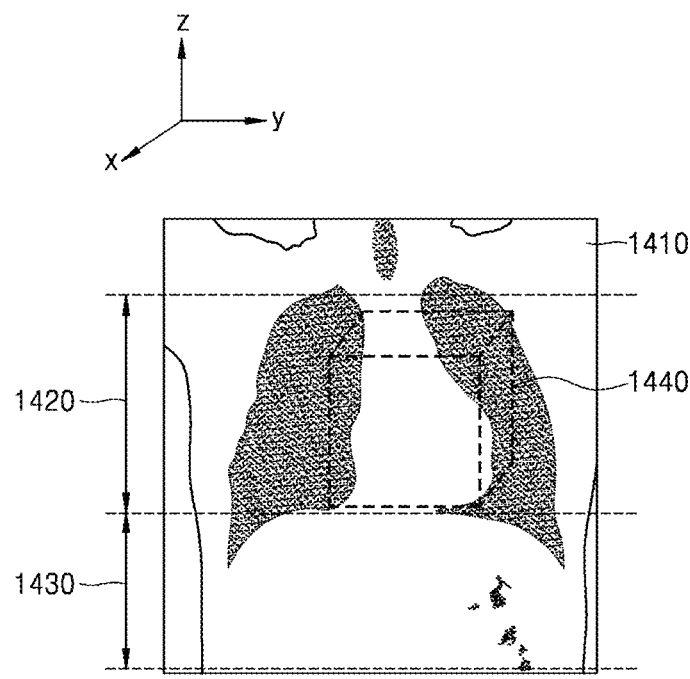
FIG. 14 is a view for explaining a process of setting motion correction parameters according Z-axis sections, according to an embodiment of the present disclosure.

FIG. 14 is a view for explaining a process of setting motion correction parameters according to Z-axis sections, according to an embodiment.

According to an embodiment, motion correction parameters are set according to Z-axis positions according to a segmentation result. For example, as shown in FIG. 14, a medical image processing apparatus may use a first parameter setting for a first Z-axis section 1420 including the heart, and may use a second parameter setting for a second Z-axis section 1430 corresponding to the abdomen other than the heart.

According to an embodiment, a volume 1440 indicating each body part is set according to a segmentation result, and motion correction parameters may be set for the volume 1440. In this case, motion correction parameters set for raw data about a Z-axis section corresponding to the volume 1440 may be used. For example, the volume 1440 corresponding to the heart may be set, a volume corresponding to the lung may be set, and a volume corresponding to the abdomen including the diaphragm may be set.

Figure 15:
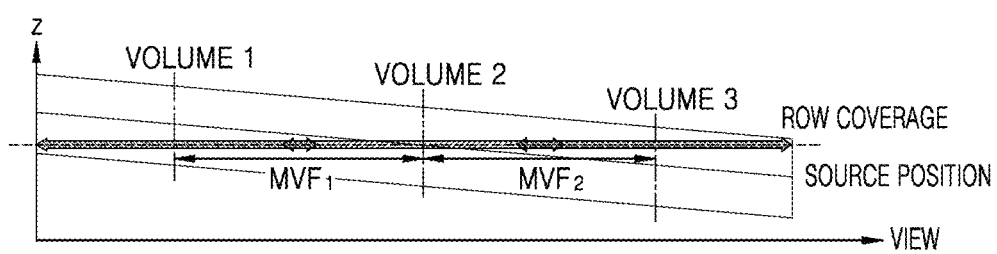
FIG. 15 is a graph for explaining a process of obtaining motion information in a second parameter setting, according to an embodiment of the present disclosure.

FIG. 15 is a graph for explaining a process of obtaining motion information in a second parameter setting according to an embodiment.

When a second parameter setting is used, motion information may be obtained by using two or more comparative images having an arbitrary angle difference therebetween. For example, as shown in FIG. 15, by using first raw data (volume 1) corresponding to a first viewpoint, second raw data (volume 2) corresponding to a second viewpoint, and third raw data (volume 3) corresponding to a third viewpoint, motion information MVF1 between the first and second viewpoints and motion information MVF2 between the second and third viewpoints may be obtained. The first raw data, the second raw data, and the third raw data may have angular sections overlapping with each other. The first raw data, the second raw data, and the third raw data may have angular sections equal to or greater than 180° and less than 360°. According to the present embodiment, since motion information about a certain time interval (duration) may be obtained, motion information at a target viewpoint may be accurately obtained without estimating the motion information through interpolation or the like. For example, a medical image processing apparatus may calculate the motion information MVF1 and MVF2 by using the first raw data (volume 1) and the second raw data (volume 3) of previous and subsequent viewpoints having a row coverage range including a Z-axis position corresponding to a target slice (volume 2) and may correct motion artifacts at the target slice (volume 2) by using the motion information MVF1 and MVF2. According to the present embodiment, since motion information to an arbitrary phase may be calculated by using interpolation or the like, a target slice may be arbitrarily selected.

According to the one or more embodiments, motion artifacts of a medical image may be reduced.

Also, according to the one or more embodiments, motion correction performance may be improved by differently setting parameters used for motion correction according to motion characteristics of an object.

The above-described embodiments of the present disclosure may be embodied in form of a computer-readable recording medium for storing computer executable command languages and data. Also, the above-described embodiments of the present disclosure may be embodied in form of a computer program product including the computer-readable recording medium for storing computer executable command languages of a plurality of instructions. The command languages may be stored in form of program codes and, when executed by a processor, may perform a certain operation by generating a certain program module. Also, when executed by a processor, the command languages may perform certain operations of the disclosed embodiments.

While embodiments of the present disclosure have been particularly shown and described with reference to the accompanying drawings, it will be understood by those of ordinary skill in the art that various changes in form and details may be made therein without departing from the spirit and scope of the invention as defined by the appended claims. The disclosed embodiments should be considered in descriptive sense only and not for purposes of limitation.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. An apparatus for processing a medical image, the apparatus comprising:

a data obtaining circuit configured to obtain raw data generated by imaging an object; and a processor, comprising a circuitry, configured to:
receive the obtained raw data from the data obtaining circuit,
based on motion characteristics of the object including a motion direction and a motion magnitude, determine motion correction parameters corresponding to an angle of raw data,
reconstruct an image to be used to obtain motion information from raw data of the angle corresponding to the motion correction parameters,
obtain the motion information by using the image reconstructed based on the determined motion correction parameters, and
reconstruct a tomography image from the raw data by using the motion information, wherein the motion correction parameters comprise a first parameter setting for reconstructing an image by using raw data of an angular section greater than 0° and less than 180° and a second parameter setting for reconstructing an image by using raw data of an angular section equal to or greater than 180° and equal to or less than 360°, and wherein the processor is further configured to:
measure a motion of the object based on the raw data;
use the first parameter setting when a magnitude or a speed of the motion is less than a reference value; and
use the second parameter setting when the magnitude or the speed of the motion is equal to or greater than the reference value.

2. The apparatus of claim 1, wherein the motion correction parameters comprise at least one from among an angular section and a time interval duration of raw data to be used to construct the image to be used to obtain the motion information.

3. The apparatus of claim 1, wherein the processor is further configured to determine the motion characteristics of the object based on at least one from among the raw data and a type of a protocol performed when the object is imaged.

4. The apparatus of claim 1, wherein the motion characteristics of the object comprise a main motion direction of the object.

5. The apparatus of claim 4, wherein the processor is further configured to measure the main motion direction of the object by comparing at least two pieces of projection data of different viewpoints.

6. The apparatus of claim 1, wherein the processor is further configured to:
use the first parameter setting when a protocol performed when the object is imaged is a protocol for imaging a heart; and
use the second parameter setting when the protocol used when the object is imaged is a protocol for imaging a lung or an abdomen.

7. The apparatus of claim 1, wherein the processor is further configured to:
use at least one pair of comparative images having an angle difference of 180° therebetween when the first parameter setting is used; and
use at least two comparative images having an angle difference greater than 0° and less than 360° therebetween when the second parameter setting is used.

8. The apparatus of claim 7, wherein a target phase is located between phases of the at least two comparative images.

9. The apparatus of claim 1, wherein the processor is further configured to:
segment the raw data or an image obtained by reconstructing the raw data; and
determine the motion correction parameters according to regions based on a segmentation result.

10. The apparatus of claim 1, wherein the processor is further configured to determine the motion correction parameters according to Z-axis positions based on a segmentation result.

11. A method of processing a medical image, the method comprising:
obtaining raw data generated by imaging an object;
determining motion correction parameters corresponding to an angle of raw data, based on motion characteristics of the object including a motion direction and a motion magnitude;
reconstructing an image to be used to obtain motion information from raw data of the angle corresponding to the motion correction parameters;
obtaining the motion information by using the image reconstructed based on the determined motion correction parameters; and
reconstructing a tomography image from the raw data by using the motion information,
wherein the motion correction parameters comprise a first parameter setting for reconstructing an image by using raw data of an angular section greater than 0° and less than 180° and a second parameter setting for reconstructing an image by using raw data of an angular section equal to or greater than 180° and equal to or less than 360°, and
wherein determining of the motion correction parameters comprises:
measuring a motion of the object based on the raw data; and
using the first parameter setting when a magnitude or a speed of the motion is less than a reference value and using the second parameter setting when the magnitude or the speed of the motion is equal to or greater than the reference value.

12. The method of claim 11, wherein the motion correction parameters comprise at least one from among an angular section and a time interval duration of raw data to be used to reconstruct the image to be used to obtain the motion information.

13. The method of claim 11, further comprising measuring the motion characteristics of the object based on at least one from among the raw data and a type of a protocol performed when the object is imaged.

14. The method of claim 11, wherein the motion characteristics of the object comprise a main motion direction of the object.

15. The method of claim 14, further comprising measuring the main motion direction of the object by comparing at least two pieces of projection data of different viewpoints.

16. The method of claim 11, wherein determining of the motion correction parameters comprises:
using the first parameter setting when a protocol performed when the object is imaged is a protocol for imaging a heart; and
using the second parameter setting when the protocol used when the object is imaged is a protocol for imaging a lung or an abdomen.

17. The method of claim 11, further comprising determining the motion correction parameters according to Z-axis positions based on a segmentation result.

18. A computer program product including a non-transitory computer-readable recording medium storing a plurality of instructions for executing a method of processing a medical image, and that, when read and executed by a processor, cause the processor to:
obtain raw data generated by imaging an object;
determine motion correction parameters corresponding to an angle of raw data, based on motion characteristics of the object including a motion direction and a motion magnitude;
reconstruct an image to be used to obtain motion information from raw data of the angle corresponding to the motion correction parameters;
obtain the motion information by using the image reconstructed based on the determined motion correction parameters; and
reconstruct a tomography image from the raw data by using the motion information,
wherein the motion correction parameters comprise a first parameter setting for reconstructing an image by using raw data of an angular section greater than 0° and less than 180° and a second parameter setting for reconstructing an image by using raw data of an angular section equal to or greater than 180° and equal to or less than 360°, and
wherein determining of the motion correction parameters comprises:
measuring a motion of the object based on the raw data; and
using the first parameter setting when a magnitude or a speed of the motion is less than a reference value and using the second parameter setting when the magnitude or the speed of the motion is equal to or greater than the reference value.

* * * * *